US008741363B2

(12) United States Patent
Albrecht et al.

(10) Patent No.: US 8,741,363 B2
(45) Date of Patent: Jun. 3, 2014

(54) SURFACTANT-CONTAINING PREPARATION COMPRISING LICOCHALCONE A

(75) Inventors: Harald Albrecht, Hamburg (DE); Svenja Cerv, Hamburg (DE); Albrecht Doerschner, Hamburg (DE); Ludger Kolbe, Dohren (DE); Jörg Kuether, Halstenbek (DE); Christopher Mummert, Bienenbüttel (DE); Stephan Ruppert, Hamburg (DE); Maren Wilken, Norderstedt (DE)

(73) Assignee: Beiersdorf AG, Hamburg (DE)

( * ) Notice: Subject to any disclaimer, the term of this patent is extended or adjusted under 35 U.S.C. 154(b) by 102 days.

(21) Appl. No.: 11/004,650

(22) Filed: Dec. 3, 2004

(65) Prior Publication Data

US 2005/0201967 A1    Sep. 15, 2005

(51) Int. Cl.
*A61K 36/484* (2006.01)

(52) U.S. Cl.
CPC .................................. *A61K 36/484* (2013.01)
USPC ........................................................ 424/757

(58) Field of Classification Search
USPC .................................. 424/725; 514/680, 724
See application file for complete search history.

(56) References Cited

U.S. PATENT DOCUMENTS

| | | | |
|---|---|---|---|
| 6,338,855 B1 * | 1/2002 | Albacarys et al. ............ | 424/409 |
| 6,342,208 B1 * | 1/2002 | Hyldgaard et al. ............ | 424/59 |
| 2002/0054918 A1 * | 5/2002 | Murad ........................... | 424/616 |
| 2005/0037042 A1 | 2/2005 | Dieck et al. | |
| 2005/0048007 A1 | 3/2005 | Ruggles | |
| 2005/0136139 A1 | 6/2005 | Kruse et al. | |
| 2005/0158259 A1 | 7/2005 | Kropke et al. | |
| 2005/0158350 A1 | 7/2005 | Max et al. | |
| 2005/0186295 A1 | 8/2005 | Stab et al. | |
| 2005/0191266 A1 | 9/2005 | Raschke et al. | |

FOREIGN PATENT DOCUMENTS

| | | | |
|---|---|---|---|
| JP | 02204495 A  * | 8/1990 | |
| JP | 10-077221 A | 3/1998 | |
| JP | 10077221 A  * | 3/1998 | |
| JP | 2001-163718 A | 6/2001 | |
| JP | 2002363054 A  * | 12/2002 | |
| JP | 2003-238379 A | 8/2003 | |
| JP | 2003238379 A  * | 8/2003 | |
| WO | WO-00/13685 A1 | 3/2000 | |
| WO | WO-03/015808 A1 | 2/2003 | |
| WO | WO 03015808 A1 * | 2/2003 | |

OTHER PUBLICATIONS

Fukai, T.; Murumo, A.; Kaitou, K.; Kanda, T.; Terada, S.; Nomura T. Abstract. "Anti-*Heicobacter pylori* flavonoids from licorice extract". Life Sci. 2002; 71(12): 1449-1463.*

'Department Dermocosmetics: Guidelines "Dermocosmetics for the Cleansing of Dry Skin"'. Jan. 22, 2001, Invernet Archive Date: Jul. 14, 2001 [retrived on Aug. 14, 2007]. Retrieved from the Internet: <URL:http://web.archive.org/web/*/http://www.gd-online.de/english/fgruppen_e/kosmetik_e/trockenhaut_e.htm> p. 3.*

'Department Dermocosmetics: Guidelines "Dermocosmetics for the Cleansing of Dry Skin"'. Jan. 22, 2001, Invernet Archive Date: Jul. 14, 2001 [retrived on Aug. 14, 2007]. Retrieved from the Internet: <URL:http://web.archive.org/web/*/http://www.gd-online.de/english/fgruppen_e/kosmetik_e/trockenehaut_e.htm> p. 3.*

Tsukiyama R, Katsura H, Tokuriki N, Kobayashi M. 'Antibacterial activity of licochalcone A against spore-forming bacteria' Antimicrob Agents Chemother. vol. 46, No. 5 (May 2002)1226-1230.*

Hunter et al. "Safety to human skin of Cocoamidopropyl Betaine: A Mild Surfactant for Personal-Care Products". Journal of Surfactants and Detergents, vol. 1, No. 2 (Apr. 1998) 235-239.*

"Sodium Lauryl Sulfate and Sodium Laureth Sulfate". Retrieved from the Internet on: Jun. 21, 2010. Retrieved from: <http://www.cosmeticsinfo.org/HBI/20>.*

(U1) "Surface-Tension Properties of Hyaluronic Acid". Journal of Glaucoma, vol. 4, Issue 3 (Jun. 1995) Abstract only.*

(V1) PureBulk: Bulk Hyaluronic Acid (Na Hyaluronate)). Retrieved from the Internet on: Mar. 21, 2011. Retrieved from the Internet: <URL: http://purebulk.com/hyaluronic-acid-na-hyaluronate>.*

(W1) "The no shampoo alternative". Retrieved from the Internet on: Mar. 21, 2011. Retrieved from the Internet: <URL: http://www.naturemoms.com/no-shampoo-alternative.html>.*

(X1) Oto et al. JP 2002-363054 A1. English translation provided by FLS, Inc. Translation Date: Jan. 2011.*

(U1) Disop. "The restorative power or sodium hyaluronate". [Retrieved on: Oct. 14, 2011]. Retrieved from the Internet: <URL: http://www.disop.com/pdf/mp/comfort_drops_hya_en.pdf>.*

(V1) "Wetting agent". WordNet, Farlex. © 2003-2008 Princeton University, Farlex Inc. Retrieved on: Oct. 14, 2011. Retrieved from the Internet: <URL: http://www.thefreedictionary.com/wetting+agent>.*

(W1) "Contact Lens Spectrum". [Retrieved on: Oct. 14, 2011] Retrieved from the Internet: <URL: http://www.clspectrum.com/article.aspx?article=13005>.*

(X1) Amurie Toxin-free eco-friendly products "Toxic ingredients to avoid in personal care products". © 2009 [Retrieved on: Oct. 14, 2011]. Retrieved from the Internet: <URL: http://www.amurie.com/learn_avoid1.html>.*

(U2) EWG's Skin Deep Cosmetics Database. "Butylene glycol" Copyright 2011 [Retrieved on: Oct. 24, 2011]. Retreived from the Internet: <URL:http://www.ewg.org/skindeep/ingredient.php?ingred06=700861>.*

(V2) Acme-Hardesty "Stearic acid 70%" [Retrieved on: Oct. 14, 2011]. Retrieved from the Internet: <URL: http://www.acme-hardesty.com/product_categories/soaps%20and%20detergents>.*

(Continued)

*Primary Examiner* — Amy L Clark

(74) *Attorney, Agent, or Firm* — Abel Law Group, LLP

(57) ABSTRACT

Cosmetic hair- and/or body-cleansing compositions comprising licochalcone A or an extract of Radix *Glycyrrhiza inflata* and one or more surfactants and, optionally, further comprising cosmetic and/or dermatological active ingredients, auxiliaries and additives.

23 Claims, No Drawings

(56) References Cited

OTHER PUBLICATIONS (W2) "Discovery Health 'How does searic acid work in skin cleansers'". [Retrieved on: Oct. 14, 2011]. Retrieved from the Internet: <URL: http://health.howstuffworks.com/skin-care/cleansing/products/stearic-acid-in-skin-cleansers.htm>.*

(X2) "Surfactant—Glyceryl monostearate-GMS" [Retrieved on: Oct. 14, 2011]. Retrieved from the Internet: <URL http://www.alibaba.com/product-gs/446103019/surfactant_Glyceryl_monostearate_GMS.html?s=p>.*

U.S. Appl. No. 10/571,530, filed Mar. 10, 2006 and entitled "Use of licochalcone A or of an extract containing licochalcone A from radix glycyrrhizae inflatae against aging skin".

U.S. Appl. No. 10/581,271, filed Jun. 1, 2006 and entitled "Combination of 2,3-dibenzylbutyrolactone and licochalcone-A".

U.S. Appl. No. 11/514,214, filed Sep. 1, 2006 and entitled "Active substance combination of licochalcone A and phenoxyethanol".

U.S. Appl. No. 11/586,538, filed Oct. 26, 2006 and entitled "Use of licochalcone A against rosacea".

Barfod L., et al., "Chalcones from Chinese Liquorice Inhibit Proliferation of T Cells and Production of Cytokines," *Int. Immunopharmacol.*, 2002, vol. 2(4), pp. 545-555.

Graf, J., "Herbal Anti-Inflammatory Agents for Skin Disease," *Skin Therapy Letter*, 2000, vol. 5(4), pp. 3-5.

Kobayashi S., et al., "Inhibitory Effect of Isoliquiritin, a Compound in Licorice Root, on Angiogenesis In Vivo and Tube Formation In Vitro," *Biol. Pharm. Bull.*, 1995, vol. 18(10), pp. 1382-1386.

Tsutsumi T., et al., "Introduction to New Functions of Natural Plant Extracts and Their Application to Cosmetics," *Fragrance Journal*, 2001, vol. 29(1), pp. 93-96.

German Search Report dated Jan. 30, 2004 for German Application No. DE 103 52 367.7.

German Search Report dated Jun. 15, 2004 for German Application No. DE 103 56 869.7.

\* cited by examiner

SURFACTANT-CONTAINING PREPARATION COMPRISING LICOCHALCONE A

FIELD OF THE INVENTION

The present invention relates to a cosmetic and/or dermatological preparation with a content of licochalcone A and surfactants, in particular for improving the condition of irritated skin or scalp, for example after or during the application of such a preparation.

BACKGROUND OF THE INVENTION

The desire for a clean and cared-for appearance is probably as old as man. Bad skin and an uncared-for hair costume offer ideal breeding grounds and homes for pathogens and parasites of all types. The desire for body hygiene was continuously intensified when, in the 1960s, besides the "classical" soap, it was also possible to formulate liquid cleansing compositions with newly developed synthetic surfactants. Since this time, we can no longer imagine daily life without bathing and showering, and a large number of products for cleansing the various parts of the body are nowadays available to the consumers.

Cosmetic and/or dermatological cleansing preparations are generally applied in the form of a foam with water to the parts of the body to be cleansed. The basis of virtually all cosmetic or dermatological cleansing preparations are washing-active surfactants. Surfactants are amphiphilic substances which can dissolve organic, nonpolar substances in water. They are characterized by ambivalent behaviour towards water and lipids: the surfactant molecule comprises at least one hydrophilic group and one lipophilic group which permit the positioning at the interface between these two classes of substance. In this way, surfactants ensure a reduction in the surface tension of the water, wetting of the skin, easier soil removal and dissolution, easy rinsing and—if desired—also foam regulation. The basis for the soil removal of lipid-containing soiling is thus given.

The hydrophilic moieties of a surfactant molecule are mostly polar functional groups, for example —COO$^-$, —OSO$_3^2$, and —SO$_3^-$, whereas the hydrophobic moieties are generally nonpolar hydrocarbon radicals. Surfactants are generally classified according to type and charge of the hydrophilic molecule moiety. In this regard, it is possible to differentiate between four groups:

anionic surfactants,
cationic surfactants,
amphoteric surfactants and
nonionic surfactants.

Most cosmetic and dermatological cleansing preparations are in the form of liquids of greater or lesser viscosity (cleaning washes, gels, and milks) or in the form of a solid (e.g. soap and washing synthetics). They are generally applied using the hands or fingers to the skin or the skin appendages (e.g. hair, nails).

For the cleaning of keratin fibres and/or skin, use is generally made of shampoos and shower gels and/or face cleansers which comprise surfactants or surfactant mixtures and care substances. Such surfactant-containing cleansing and/or shaving compositions (e.g. shampoos, shower gels, shaving foams, etc.) are subject to a large number of requirements which these preparations should satisfy at the same time: these preparations are expected to be skin-compatible and to leave behind a pleasant feel on the skin following application to the skin. This skin, in particular the epidermis, being a barrier organ of the human organism, is subjected to external effects to a particular degree. Such effects can exert irritation to the skin which, in people with sensitive or injured skin, can lead to reddening, tightness, burning and/or itching. Such effects include UV irradiation, mechanical stresses, and contact with irritative substances. Areas of skin which are subjected to these effects in a largely unprotected way and react sensitively include, in particular, the scalp. Besides the solar irradiation to which the scalp is exposed with greater or lesser protection depending on the hair style, mechanical stresses resulting from combing, brushing, and cutting (including shaving), the scalp is also subjected to contact with irritative substances. Besides chemicals which are used for colouring the hair or permanent waving, mention may be here in particular of the surfactants which are used during often daily hair washing. After hair washing, the hair and/or the scalp is often subjected to further treatments which care for the hair and which are intended to stimulate the scalp, but which likewise lead to the described undesired effects.

The surfactants and surfactant mixtures used are composed of anionic, amphoteric and/or nonionic surfactants. The usual use concentrations of the surfactants up to about 25% and the application conditions customary for body- and hair-cleansing, modern shampoo compositions have good skin compatibility. Nevertheless, in the case of a sensitive scalp or increased use (sportsman), scalp irritations may result. The use of relatively small use concentrations or relatively mild surfactants does not represent a solution to this problem since losses in performance with regard to the foaming ability and the foam creaminess are always also associated with it.

Moreover, the formulations should be easy to foam and form a creamy, finely bubbled foam. However, such preparations as the prior art have the disadvantage that they fulfil these requirements in an only inadequately consistent manner. Good foaming products are generally less skin-friendly and leave behind a dry feel on the skin. Especially mild, skin-friendly products, in turn, generally do not foam well.

A further disadvantage of the prior art consists in the fact that, particularly in industrialized countries, there is an increase amongst the population in incompatibilities and allergic reactions towards a large number of chemicals and ingredients of cosmetics and dermatological compositions. Surfactant-containing cosmetic and dermatological preparations are also being affected by this development to an increasing degree since they can sometimes partly dissolve the protective lipid layer on the skin and, on the one hand, penetrate deep into the skin, on the other hand remain on the skin for a long time. For this reason, the concentration of surfactants in cosmetic and/or dermatological preparations should be kept as low as possible. In addition, there is a need for surfactant-containing preparations with varying surfactant composition since incompatibilities and allergic reactions are substance-specific and the people affected are thus given the option of using cosmetic and/or dermatological preparations with a composition which is matched to their incompatibility profile.

SUMMARY OF THE INVENTION

The object of the present invention was to overcome, or at least significantly reduce, the shortcomings of the prior art of surfactant-containing cosmetic and/or dermatological preparations, in particular of hair shampoos, shower gels, and shaving foams. The aim was to develop preparations which are skin-friendly and leave behind a pleasant feel (soft, cared for, smooth, clean) on the skin. At the same time, these preparations should foam easily and form a creamy, fine-bubbled, dense, stable foam.

Licochalcone A is a constituent of the extract from Radix *Glycyrrhizae inflatae* and is characterized by the following structure:

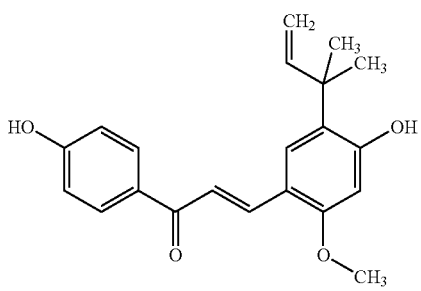 [SMILES: C=CC(C)(C)c1cc(/C=C/C(=O)c2ccc(O)cc2)c(OC)cc1O]

Like the liquorice (Glycyrrhiza glabra) approved within Europe, the plant species *Glycyrrhizae inflatae* belongs to the genus *Glycyrrhiza*, which belongs to the *Fabaceae* family (pea plants).

It has now been found, in a manner which is surprising and unforeseeable by the person skilled in the art, that cosmetic hair- and/or body-cleansing compositions comprising licochalcone A or an extract of Radix *Glycyrrhizae inflatae* and one or more surfactants, besides, if appropriate, further cosmetic and/or dermatological active ingredients, auxiliaries and additives, overcome the disadvantages of the prior art. By means of such preparations, the skin or scalp which comes into contact with the compositions during use is cared for in a particular way by improving the condition of irritated skin or scalp. The cause of irritated skin or scalp may be UV irradiation, mechanical stress and/or contact with chemicals. Contact with chemicals and in this connection mention is to be made quite specifically of frequent contact with cleansing surfactants, is a common stress factor for the skin or scalp, whose symptoms, such as reddening, burning, itching, are significantly reduced or eliminated by the products according to the invention without influencing the care properties and the quality and distributability of the composition in an adverse way. A condition improved in this way can be observed particularly in the case of surfactant-damaged skin or scalp.

DETAILED DESCRIPTION OF THE INVENTION

The extract of Radix *Glycyrrhizae inflatae* may be aqueous or alcoholic. The alcoholic extract is particularly preferred due to its effectiveness. Such extracts are obtainable, for example, under the names "Polyol Soluble Licorice Extract P-U" or "Aqua Licorice Extract P-U" from Maruzen Pharmaceuticals. The first-mentioned extract is an alcoholic extract which is in powder form. "Aqua Licorice Extract P-U" also comprises additional ethoxylated and/or propoxylated raw materials. In this connection, it is advantageous if these ethoxylated and/or propoxylated raw materials, which are added to the extracts by the manufacturer for various reasons, are not present in the preparation because their possible sensitizing potential can then not arise. In particular, the absence of PPG-6 (Nikkol PEN) is of great advantage. It is very particularly advantageous to start from an alcoholic extract, as can be obtained under the name Polyol Soluble Licorice Extract PU (INCI name Glycyrrhiza Inflata) from Maruzen. The extract of Radix *Glycyrrhizae inflatae* comprises a content of about 25% licochalcone A. It is thus possible to prepare cosmetic or dermatological preparations for body- and hair cleansing which have exceptional mildness. Beyond these effects, it was surprisingly found that the preparations according to the invention can be used advantageously for the treatment and prophylaxis of post-inflammatory skin conditions triggered by surfactant damage to the skin. Furthermore, these formulations are suitable for the treatment of skin reddening, in particular rosacea. It is preferred if the content of licochalcone A or extract of Radix *Glycyrrhizae inflatae* is at least 0.0001% by weight, particularly preferably 0.0005% by weight, very particularly preferably 0.001% by weight, very extraordinarily preferably 0.01% by weight, very extraordinarily particularly preferably 0.05% by weight and at most 10% by weight, particularly preferably 5% by weight, very particularly preferably up to 2% by weight, very extraordinarily particularly preferably 0.1% by weight, in each case based on the total weight of the preparation.

In addition, it is preferred if the surfactants used are anionic, cationic, zwitterionic, amphoteric surfactants, particularly preferably anionic and zwitterionic surfactant and/or the combination of ionic surfactants with nonionic surfactants. It is particularly preferred if the total amount of surfactants is from 1 to 50% by weight, particularly preferably 5 to 30% by weight, based on the total weight of the preparation. It is very particularly preferred if the ratio of the total amount of saccharides to the total amount of surfactants is from 1:1000 to 10:1, preferably from 1:300 to 1:1 and very particularly preferably from 1:100 to 1:5.

It is also preferred if sodium laureth sulphate is used as surfactant on its own or in combination with further surfactants, particular preference being given to the combination of sodium lauryl ether sulphate and cocoamidopropylbetaine and/or other surfactants, such as, for example, alkyl polyglucosides, amphoacetates, sulfosuccinates.

In addition, it is preferred if such a composition is stored in a foam dispenser and is applied from this. It is particularly preferred if such a composition is used as impregnation for an insoluble substrate.

Preference is also given to those compositions which are suitable as hair-cleansing compositions and additionally a polymeric quaternized ammonium salt of hydroxyethylcellulose which has been modified with a trimethylammonium-substituted epoxide (INCI: Polyquaternium-10) (Ucare Polymer JR 400 from Amerchol) and/or a depolymerized guar gum derivative which has been quaternized (INCI: Guar Hydroxypropyl Trimonium Chloride) (Jaguar Excel from Rhodia) is present in the preparation, particularly preferably in concentrations of from 0.01 to 5% by weight. Moreover, a combination of such a composition with an insoluble substrate is preferred.

The invention also comprises the use of such compositions for the treatment, in particular for improving the condition of predamaged skin or scalp, preferably skin or scalp damaged by surfactants, for the cleansing and/or care of the skin and skin appendages, as shower, foam and/or tub bath, as hair shampoo, as shaving foam, as face-cleansing preparation for the removal of decorative cosmetics, and a product comprising such a composition contained in a package on which there is writing, where the writing indicates at least one of the specified uses. Moreover, a non-therapeutic method for the treatment of skin or scalp damaged by surfactants is characterized by the topical application of such a composition.

Advantageous washing-active anionic surfactants for the purposes of the present invention are: acylamino acids and salts thereof, such as
  acyl glutamates, in particular sodium acyl glutamate
  sarcosinates, for example myristoyl sarcosinate, TEA-lauroyl sarcosinate, sodium lauroyl sarcosinate and sodium cocoyl sarcosinate; sulphonic acids and salts thereof, such as
  acyl isethionates, e.g. sodium/ammonium cocoyl isethionate,
  sulfosuccinates, for example dioctyl sodium sulfosuccinate, disodium laureth suflosuccinate, disodium lauryl sulfosuccinate and disodium undecylenamido MEA sulfosuccinate, disodium PEG-5 lauryl citrate sulfosuccinate and derivatives; and
sulphuric esters, such as
  alkyl ethers sulphates, for example sodium, ammonium, magnesium, MIPA, TIPA laureth sulphate, sodium myreth sulphate and sodium $C_{12-13}$ pareth sulphate,
  alkyl sulphates, for example sodium, ammonium and TEA lauryl sulphate.
Further advantageously anionic surfactants are:
  taurates, for example sodium lauroyl taurate and sodium methyl cocoyl taurate,
  ether carboxylic acids, for example sodium laureth-13 carboxylate and sodium PEG-6 cocamide carboxylate, sodium PEG-7 olive oil carboxylate
  phosphoric esters and salts, such as, for example, DEA oleth-10 phosphate and dilaureth-4 phosphate,
  alkylsulphonates, for example sodium cocomonoglyceride sulphate, sodium $C_{12}$-$C_{14}$ olefin sulphonate, sodium lauryl sulphoacetate and magnesium PEG-3 cocoamide sulphate,
  acyl glutamates such as di-TEA palmitoyl aspartate and sodium caprylic/capric glutamate, and
  acyl peptides, for example palmitoyl hydrolysed milk protein, sodium cocoyl hydrolysed soya protein and sodium/potassium cocoyl hydrolysed collagen; and
carboxylic acids and derivatives, such as
  for example lauric acid, aluminium stearate, magnesium alkanolate and zinc undecylenate,
  ester carboxylic acids, for example calcium stearoyl lactylate, laureth-6 citrate and sodium PEG-lauramide carboxylate, and
  alkylarylsulphonates.
Advantageous washing-active cationic surfactants for the purposes of the present invention are quaternary surfactants. Quaternary surfactants comprise at least one N atom which is covalently bonded to 4 alkyl or aryl groups. For example, alkylbetaine, alkylamidopropylbetaine and alkylamidopropylhydroxy sultaine are advantageous.
Further advantageous cationic surfactants for the purposes of the present invention are also:
  alkylamines,
  alkylimidazoles and
  ethoxylated amines,
and in particular salts thereof.
Advantageous washing-active amphoteric surfactants for the purposes of the present invention are acyl/dialkylethylenediamines, for example sodium acyl amphoacetate, disodium acyl amphodipropionate, disodium alkyl amphodiacetate, sodium acyl amphohydroxypropylsulphonate, disodium acyl amphodiacetate, sodium acyl amphopropionate and N-coconut fatty acid amidoethyl-N-hydroxyethyl glycinate sodium salts.

Further advantageous amphoteric surfactants are N-alkylamino acids, for example aminopropylalkylglutamide, alkylaminopropionic acid, sodium alkylimidodipropionate and lauroamphocarboxyglycinate.
Advantageous washing-active nonionic surfactants for the purposes of the present invention are
  alkanolamides, such as cocamides MEA/DEA/MIPA,
  esters which are produced by esterification of carboxylic acids with ethylene oxide, glycerol, sorbitol or other alcohols, and
  ethers, for example ethoxylated alcohols, ethoxylated lanolin, ethoxylated polysiloxanes, propoxylated POE ethers and alkyl polyglycosides, such as lauryl glucoside, decyl glycoside and cocoglycoside.
Further advantageous nonionic surfactants are alcohols and amine oxides, such as cocoamidopropylamine oxide.
It is advantageous to choose the washing-active surfactant or surfactants according to the invention from the group of surfactants which have a HLB value of more than 25, those which have a HLB value of more than 35 being particularly advantageous.
According to the invention, it is particularly preferred if the surfactants used are anionic surfactants, it being preferred to use sodium laureth sulphate as surfactant on its own or in combination with further surfactants. Particular preference is given to these combinations if the preparation according to the invention is used in the form of a shampoo, shower gel, foam bath or tub bath, and in the form of a hand washing lotion.
According to the invention, it is advantageous if one or more surfactants is used in a concentration of from 1 to 50% by weight, preferably in a concentration of from 5 to 30% by weight and very particularly preferably in a concentration of from 10 to 20% by weight, in each case based on the total weight of the preparation.
Anionic surfactants, preferably alkyl sulphates, particularly preferably ethoxylated alkyl sulphates (lauryl ether sulphates; myristyl ether sulphates) are advantageously used according to the invention in a concentration of 1-20% by weight and preferably in a concentration of 5-12% by weight, based on the total weight of the preparation. These concentration ranges are also regarded as being preferred if the anionic surfactants used are soaps of fatty acids (carboxylic acids and derivatives), as is the case, for example, with shaving foams and gels.
Amphoteric surfactants, preferably quaternary surfactants, particularly preferably alkylamidopropylbetaine, are advantageously used according to the invention in a concentration of 1-20% by weight and preferably in a concentration of 2-10% by weight, in each case based on the total weight of the preparation.
According to the invention, preference is given to using the surfactants in combinations with LES.
According to the invention, the amphoteric surfactants used may also advantageously be acyl/dialkylethylenediamines, in particular disodium alkylamphodiacetate. For these amphoteric surfactants, the preferred concentration ranges are 1-10% by weight and particularly preferably 1-5% by weight, in each case based on the total weight of the preparation.
In addition, in accordance with the invention, polysorbates can advantageously be incorporated as washing-active agents into the preparation.
Polysorbates advantageous according to the invention are
  polyoxyethylene(20)sorbitan monolaurate (Tween 20, CAS No. 9005-64-5)

polyoxyethylene(4)sorbitan monolaurate (Tween 21, CAS No. 9005-64-5)

polyoxyethylene(4)sorbitan monostearate (Tween 61, CAS No. 9005-67-8)

polyoxyethylene(20)sorbitan tristearate (Tween 65, CAS No. 9005-71-4)

polyoxyethylene(20)sorbitan monooleate (Tween 80, CAS No. 9005-65-6)

polyoxyethylene(5)sorbitan monooleate (Tween 81, CAS No. 9005-65-5)

polyoxyethylene(20)sorbitan trioleate (Tween 85, CAS No. 9005-70-3).

Very particularly advantageous are, in particular

Polyoxyethylene(20)sorbitan monopalmitate (Tween 40, CAS No. 9005-66-7)

Polyoxyethylene(20)sorbitan monostearate(Tween 60, CAS No. 9005-67-8).

According to the invention, these are advantageously used in a concentration of from 0.1 to 5% by weight and in particular in a concentration of from 1.5 to 2.5% by weight, based on the total weight of the formulation individually or as a mixture of two or more polysorbates.

The cosmetic and/or dermatological surfactant-containing preparation according to the invention is also characterized in that the ratio of the total amount of saccharides to the total amount of surfactants is from 1:1000 to 10:1, preferably from 1:300 to 1:1 and very particularly preferably from 1:100 to 1:5.

Besides one or more water phases, the cosmetic and/or dermatological preparation according to the invention can additionally comprise one or more oil phases and, for example, be in the form of W/O emulsion (water-in-oil), W/S emulsion (water-in-silicone oil), O/W emulsion (oil-in-water), or S/W emulsion (silicone oil-in-water). In addition, according to the invention they can advantageously also be in the form of so-called multiple emulsions, such as, for example, W/O/W, O/W/O, W/S/W or S/W/S emulsions. Such formulations may preferably also be a microemulsion (e.g. a PIT emulsion), a solids emulsion (i.e. an emulsion which is stabilized by solids, e.g. a Pickering emulsion), a sprayable emulsion, or a hydrodispersion. Furthermore, the preparations for the purposes of the present invention may also be virtually anhydrous (water content below 5% by weight, based on the total weight of the preparation).

According to the invention, besides water, the preparation according to the invention can also comprise other ingredients as aqueous phase, for example alcohols, diols or polyols of low carbon number, and ethers thereof, preferably ethanol, isopropanol, propylene glycol, ethylene glycol, ethylene glycol monoethyl and monobutyl ether, propylene glycol monomethyl, monoethyl and monobutyl ether, diethylene glycol monomethyl or monoethyl ether and analogous products.

The oil phase of the preparation according to the invention, i.e. the lipophilic organic constituents, are advantageously chosen from the group of polar oils, for example from the group of lecithins and of fatty acid triglycerides, namely the triglycerol esters of saturated and/or unsaturated, branched and/or unbranched alkanecarboxylic acids of chain length from 8 to 24, in particular 12 to 18, carbon atoms. The fatty acid triglycerides can, for example, advantageously be chosen from the group of synthetic, semi-synthetic and natural oils, such as, for example, cocoaglyceride, olive oil, sunflower oil, soya oil, peanut oil, rapeseed oil, almond oil, palm oil, coconut oil, castor oil, wheatgerm oil, grapeseed oil, thistle oil, evening primrose oil, macadamia nut oil, and the like.

Also advantageous according to the invention are, for example, natural waxes of animal and vegetable origin, such as, for example, beeswax and other insect waxes, and berry wax, shea butter and/or lanolin (wool wax).

Further advantageous polar oil components can also be chosen for the purposes of the present invention from the group of esters of saturated and/or unsaturated, branched and/or unbranched alkanecarboxylic acids of chain length from 3 to 30 carbon atoms and saturated and/or unsaturated, branched and/or unbranched alcohols of chain length from 3 to 30 carbon atoms, and from the group of esters of aromatic carboxylic acids and saturated and/or unsaturated, branched and/or unbranched alcohols of chain length from 3 to 30 carbon atoms. Such ester oils can then advantageously be chosen from the group consisting of octyl palmitate, octyl cocoate, octyl isostearate, octyl dodecyl myristate, octyldodecanol, cetearyl isononoanoate, isopropyl myristate, isopropyl palmitate, isopropyl stearate, isopropyl oleate, n-butyl stearate, n-hexyl laurate, n-decyl oleate, isocotyl stearate, isonyl stearate, isononyl isononanoate, 2-ethylhexyl palmitate, 2-ethylhexyl laurate, 2-hexyldecyl stearate, 2-octyldodecyl palmitate, stearyl heptanoate, oleyl oleate, oleyl erucate, erucyl oleate, erucyl erucate, tridecyl stearate, tridecyl trimellitate, and synthetic, semisynthetic and natural mixtures of such esters, such as, for example, jojoba oil.

In addition, the oil phase can advantageously be chosen from the group of dialkyl ethers and dialkyl carbonates, for example dicaprylyl ether (Cetiol OE) and/or dicaprylyl carbonate, for example that available under the trade name Cetiol CC from Cognis, being advantageous.

It is also preferred to choose the oil component or components from the group consisting of isoeicosane, neopentyl glycol diheptanoate, propylene glycol dicaprylate/dicaprate, caprylic/capric/diglyceride succinate, butylene glycol dicaprylate/dicaprate, cocoglycerides (e.g. Myritol® 331 from Henkel), $C_{12-13}$ alkyl lactate, di-$C_{12}$-$C_{13}$ alkyl tartrate, triisostearin, dipentaerythrityl hexcaprylate/hexacaprate, propylene glycol monoiostearate, tricaprylin, dimethyl isosorbide. It is particularly advantageous if the oil phase of the formulations according to the invention has a content of $C_{12-15}$-alkyl benzoate or consists entirely of this.

Advantageous oil components are also, for example, butyloctyl salicylate (for example that available under the trade name Hallbrite BHB from CP Hall), hexadecyl benzoate and butyloctyl benzoate and mixtures thereof (Hallstar AB) and/or diethylhexyl naphthalate (Corapan® TQ from Haarmann & Reimer).

Any desired mixtures of such oil and wax components can also be used advantageously for the purposes of the present invention.

The lipid phase can comprise the polar oil components according to the invention in a concentration of up to 40% by weight, based on the total weight of the lipid phase.

In addition, the oil phase can likewise advantageously also comprise nonpolar oils, for example those which are chosen from the group of branched and unbranched hydrocarbons and hydrocarbon waxes, in particular mineral oil, Vaseline (petrolatum), paraffin oil, squalane and squalene, polyolefins, hydrogenated polysiobutenes and isohexadecane. Among the polyolefins, polydecenes and hydrogenated polyisobutenes are the preferred substances.

The oil phase can also advantageously have a content of cyclic or linear silicone oils or consist entirely of such oils, although it is preferred to use an additional content of other oil phase components apart from the silicone oil or the silicone oils.

Silicone oils are high molecular weight synthetic polymeric compounds in which silicon atoms are joined via oxygen atoms in a chain-like and/or reticular manner and the remaining valences of the silicon are saturated by hydrogen radicals (mostly methyl groups, less often ethyl, propyl, phenyl groups etc.). Systematically, the silicone oils are referred to as polyorganosiloxanes. The methyl-substituted polyorganoisiloxanes, which are the compounds of this group of most significance in terms of amount and are characterized by the following structural formula

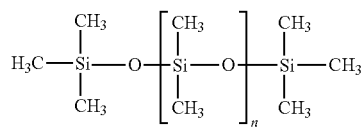

are also referred to as polydimethylsiloxane and Dimethicone (INCI). Dimethicones come in various chain lengths and with various molecular weights.

Advantageous polyorganosiloxanes for the purposes of the present invention are, for example, dimethylpolysiloxanes [poly(dimethylsiloxane)], which are available, for example, under the trades names Abil 10 to 10,000 from Th. Goldschmidt. Also advantageous are phenylmethylpolysiloxanes (INCI: Phenyl Dimethicone, Phenyl Trimethicone), cyclic silicone (octamethylcyclotetrasiloxane and decamethylcyclopentasiloxane), which are referred to according to INCI also as Cyclomethicones, amino-modified silicones (INCI: Amodimethicones) and silicone waxes, e.g. polysiloxane-polyalkylene copolymers (INCI: Stearyl Dimethicone and Cetyl Dimethicone) and dialkoxydimethylpolysiloxanes (Stearoxy Dimethicone and Behenoxy Stearyl Dimethicone), which are available as various Abil wax grades from Th. Goldschmidt. However, other silicones oils can also be used advantageously for the purposes of the present invention, for example cetyldimethicone, hexamethylcyclotrisiloxane, polydimethylsiloxane, and poly(methylphenylsiloxane).

According to the invention, it is advantageous to use the lipophilic constituents of a preparation according to the invention as refatting substances. Refatting substances which can be used advantageously are, for example, purcellin oil, Eucerti® and Neocerit®.

In addition, according to the invention, it is advantageous if thickeners are used in the preparations according to the invention. These can, for example, advantageously be chosen from further compounds of the group of gums.

The gums include plant or tree saps which harden in the air and form resins or extracts of aquatic plants. For the purposes of the present invention, from this group it is advantageous to choose, for example, gum arabic, carob seed flour, tragacanth, karaya, guar gum, pectin, gellan gum, carrageen, agar, algins, chondrus, and xanthan gum.

Also advantageous is the use of derivatized gums, such as, for example, hydroxypropyl guar (Jaguar® HP 8).

Also advantageous according to the invention is the use of polysaccharides and polysaccharide derivatives. Among the polysaccharides and polysaccharide derivatives, hyaluronic acid, chitin and chitosan, chondroitin sulphates, starch and starch derivatives, for example, are thickeners advantageous according to the invention.

Also advantageous according to the invention is the use of cellulose derivatives. Among the cellulose derivatives, methylcellulose, carboxymethylcellulose, hydroxyethylcellulose, hydroxypropylmethylcellulose, for example, are thickeners advantageous according to the invention.

Also advantageous according to the invention is the use of sheet silicates. The sheet silicates include naturally occurring and synthetic clay earths, such as, for example, montmorillonite, bentonite, hectorite, laponite, magnesium aluminium silicates, such as Veegum®. These can be used as they are or in modified form as thickeners, such as, for example, stearylalkonium hectorite.

In addition, silica gels can also be used advantageously.

Also advantageous according to the invention is the use of polyacrylates. The polyacrylates include, for example, Carbopol grades from Noveon (Carbopol 980, 981, 1382, 5984, 2984, ETD 2001, ETD 2020, ETD 2050 or Pemulen TR1 & TR2).

Also advantageous according to the invention is the use of polymers. The polymers include, for example, polyacrylamides (Seppigel 305), polyvinyl alcohols, PVP, PVP/VA copolymers, polyglycols.

According to the invention, it is advantageous to use one or more thickeners in a concentration of from 0.1 to 5% by weight, based on the total weight of the preparation.

In addition, according to the invention, it may be advantageous if, in the preparations according to the invention, salts are used for thickening the preparation such that preparations with viscosities of from 2000 mPas to 6000 mPas can be prepared. Salts are understood as meaning mono- or polyvalent alkali metal compounds or alkaline earth metal compounds with halogen anions. Particular preference is given to using sodium chloride.

According to the invention, it is advantageous to use one or more alkali metal salts or alkaline earth metal salts in a concentration of from 0.1 to 3% by weight, based on the total weight of the preparation.

According to the invention, the preparation according to the invention can advantageously comprise one or more preservatives. Advantageous preservatives for the purposes of the present invention are, for example, formaldehyde donors (such as e.g. DMEM Hydantoin, which is available, for example, under the trade name Glydant™ from Lonza), iodopropyl butylcarbamates (e.g. those available under the trade names Glycacil-L, Glycacil-S from Lonza and/or Dekaben LMB from Jan Dekker), parabens (i.e. alkyl p-hydroxybenzoates, such as methyl-, ethyl-, propyl- and/or butylparaben), phenoxyethanol, ethanol, benzoic acid and the like. According to the invention, the preservative system usually further advantageously also comprises preservative auxiliaries, such as, for example, octoxyglycerol, glycine soya etc.

The table below gives an overview of some preservatives advantageous according to the invention:

| | |
|---|---|
| E 200 | Sorbic acid |
| E 201 | Sodium sorbate |
| E 202 | Potassium sorbate |
| E 203 | Calcium sorbate |
| E 210 | Benzoic acid |
| E 211 | Sodium benzoate |
| E 212 | Potassium benzoate |
| E 213 | Calcium benzoate |
| E 214 | Ethyl p-hydroxybenzoate |
| E 215 | Ethyl p-hydroxybenzoate Na salt |
| E 216 | n-Propyl p-hydroxybenzoate |
| E 217 | n-Propyl p-hydroxybenzoate Na salt |
| E 218 | Methyl p-hydroxybenzoate |
| E 219 | Methyl p-hydroxybenzoate Na salt |
| E 220 | Sulphur dioxide |
| E 221 | Sodium sulphite |
| E 222 | Sodium hydrogensulphite |
| E 223 | Sodium disulphite |
| E 224 | Potassium disulphite |

| | |
|---|---|
| E 226 | Calcium sulphite |
| E 227 | Calcium hydrogensulphite |
| E 228 | Potassium hydrogensulphite |
| E 230 | Biphenyl (diphenyl) |
| E 231 | Orthophenylphenol |
| E 232 | Sodium orthophenylphenoxide |
| E 233 | Thiabendazole |
| E 235 | Natamycin |
| E 236 | Formic acid |
| E 237 | Sodium formate |
| E 238 | Calcium formate |
| E 239 | Hexamethylenetetramine |
| E 249 | Potassium nitrite |
| E 250 | Sodium nitrite |
| E 251 | Sodium nitrate |
| E 252 | Potassium nitrate |
| E 280 | Propionic acid |
| E 281 | Sodium propionate |
| E 282 | Calcium propionate |
| E 283 | Potassium propionate |
| E 290 | Carbon dioxide |

Also advantageous are preservatives or preservative auxiliaries customary in cosmetics, such as dibromodicyanobutane (2-bromo-2-bromomethylglutarodinitrile), phenoxyethanol, 3-iodo-2-propynyl butylcarbamate, 2-bromo-2-nitropropane-1,3-diol, imidazolidinylurea, 5-chloro-2-methyl-4-isothiazolin-3-one, 2-chloroacetamide, benzalkonium chloride, benzyl alcohol, salicylic acid and salicylates.

Here, it is particularly preferred according to the invention if the preservatives used are iodopropyl butylcarbamates, parabens (methyl-, ethyl-, propyl- and/or butylparaben) and/or phenxoyethanol.

According to the invention, one or more preservatives in a concentration of 2% by weight or less than 2% by weight, preferably 1.5% by weight or less than 1.5% by weight and particularly preferably 1% by weight or less than 1% by weight, in each case based on the total weight of the preparation, are advantageous according to the invention.

The preparation according to the invention advantageously comprises one or more conditioners. Conditioners preferred according to the invention are, for example, all compounds which are listed in the *International Cosmetic Ingredient Dictionary and Handbook* (Volume 4, Editor: R. C. Pepe, J. A. Wenninger, G. N. McEwen, The Cosmetic, Toiletry and Fragrance Association, 9th edition, 2002) under section 4 under the keywords Hair Conditioning Agents, Humectants, Skin-Conditioning Agents, Skin-Conditioning Agents-Emollient, Skin-Conditioning Agents-Humectant, Skin-Conditioning Agents-Miscellaneous, Skin-Conditioning Agents-Occlusive and Skin Protectants, and all of the compounds listed in EP 0934956 (pp. 11-13) under water soluble conditioning agent and oil soluble conditioning agent. Some of these compounds are listed by name under the constituents of the aqueous phase and of the oil phase. Further conditioners advantageous according to the invention represent, for example, the compounds named Polyquaternium according to the international nomenclature of cosmetic ingredients (INCI) (in particular Polyquaternium-1 to Polyquaterium-56).

Conditioners advantageous according to the invention from the group of Polyquaterium compounds may be chosen here, for example, from the compounds listed in the table.

| INCI name | CAS number | Polymer type | Example (trade name) |
|---|---|---|---|
| Polyquaternium-2 | CAS 63451-27-4 | Urea, N,N'-bis[3-(dimethylamino)propyl] polymer with 1,1'-oxybis(2-chloroethane) | Mirapol ® A-15 |
| Polyquaternium-5 | CAS 26006-22-4 | Acrylamide, β-methacryloxethyltriethyl-ammonium methosulphate | |
| Polyquaternium-6 | CAS 26062-79-3 | N,N-dimethyl-N-2-propenyl-2-propenaminium chloride | Merquat ® 100 |
| Polyquaternium-7 | CA 26590-05-6 | N,N-dimethyl-N-2-propenyl-2-propenaminium chloride, 2-propenamide | Merquat ® S |
| Polyquaternium-10 | CAS 53568-66-4, 55353-19-0, 54351-50-7, 68610-92-4, 81859-24-7 | Quaternary ammonium salt of hydroxyethylcellulose | Celquat ® SC-230M |
| Polyquaternium-11 | CAS 53633-54-8 | Vinylpyrrolidone/dimethylaminoethyl methacrylate copolymer/diethyl sulphate reaction product | Gafquat ® 755N |
| Polyquaternium-16 | CAS 29297-55-0 | Vinylpyrrolidone/vinylimidazolinium methochloride copolymer | Luviquat ® HM552 |
| Polyquaternium-17 | CAS 90624-75-2 | | Mirapol ® AD-1 |
| Polyquaternium-19 | CAS 110736-85-1 | Quaternized water-soluble polyvinyl alcohol | |
| Polyquaternium-20 | CAS 110736-86-2 | Quaternized polyvinyl octadecyl ether dispersible in water | |
| Polyquaternium-21 | | Polysiloxane-polydimethyldimethyl-ammonium acetate copolymer | Abil ® B 9905 |
| Polyquaternium-22 | CAS 53694-17-0 | Dimethyldiallylammonium chloride/acrylic acid copolymer | Merquat ® 280 |
| Polyquaternium-24 | CAS 107987-23-5 | Polymeric quaternary ammonium salt of hydroxyethylcellulose | Quartisoft ® LM-200 |
| Polyquaternium-28 | CAS 131954-48-8 | Vinylpyrrolidone-methacrylamido-propyltrimethylammonium chloride copolymer | Gafquat ® HS-100 |

-continued

| INCI name | CAS number | Polymer type | Example (trade name) |
|---|---|---|---|
| Polyquaternium-29 | CAS 92091-36-6, 148880-30-2 | Chitosan which has been reacted with propylene oxide and quaternized with epichlorohydrin | Lexquat ® CH |
| Polyquaternium-31 | CAS 136505-02-7, 139767-67-7 | Polymeric quaternary ammonium salt which is prepared by reacting DMAPA acrylate/acrylic acid/acrylonitrogens copolymers and diethyl sulphate | Hypan ® QT 100 |
| Polyquaternium-32 | CAS 35429-19-7 | N,N,N-treimethyl-2-{[82-methyl-1-oxo-2-propneyl)oxy]ethanaminium chloride, polymer with 2-propenamide | |
| Polyquaternium-37 Polyquaternium-44 | CAS 26161-33-1 | Copolymeric quaternary ammonium salt of vinylpyrrolidone and quaternized imidazoline | |

The cosmetic preparations advantageous according to the invention are characterized in that the guar hydroxypropylt-rimethylammonium chlorides have a charge density of from 0.4 to 1.0 meq/g, and a molecular weight of from 100,000 to 1,800,000. Guar hydroxypropyltrimethylammonium chlorides preferred according to the invention originate from the Jaguar series, particular preference being given according to the invention to the product Jaguar Excel from Rhodia.

According to the invention, it is advantageous to use one or more guar hydroxypropyltrimethylammonium chlorides in a concentration of from 0.01 to 10% by weight, preferably in a concentration of from 0.01 to 2% by weight and very particularly preferably in a concentration of from 0.01 to 0.5% by weight, in each case based on the total weight of the preparation. For the purposes of the present invention, it is advantageous to use polyquatemium-10 in a concentration of from 0.01 to 2% by weight, preferably in a concentration of from 0.05 to 1.5% by weight and particularly preferably from 0.1 to 1.0% by weight, in each case based on the total weight of the preparation. Furthermore, it is advantageous for the purposes of the present invention to use guar hydroxypropyltrimethy-lammonium chloride in combination with polyquatemium-10 in concentration ratios of from 1:10 to 10:1.

It is also in the meaning of the present invention to add pearlescent pigments, mica and/or effect pigments to the preparation according to the invention in order to make the preparation more visually attractive.

According to the invention, the preparations according to the invention may advantageously comprise one or more UV light protection filters. Particularly advantageous UV filter substances liquid at room temperature for the purposes of the present invention are homomenthyl salicylate (INCI: Homosalate), 2-ethylhexyl 2-cyano-3,3-diphenylacrylate (INCI: Octocrylene), 2-ethylhexyl 2-hydroxybenzoate (2-ethylhexyl salicylate, octyl salicylate, INCI: Ethylhexyl Salicylate) and esters of cinnamic acid, preferably 2-ethylhexyl 4-methoxycinnamate (INCI: Ethylhexyl Methoxycinnamate) and isopentyl 4-methoxycinnamate (INCI: Isoamyl p-Methoxycinnamate) and polymeric UV filters, such as the (3-(4-(2,2-bisethoxycarbonylvinyl)phenoxy)propenyl)-methylsi-loxane/dimethylsiloxane copolymer which is available, for example, from Hoffman-La Roche under the trade name Parsol SLX.

Preferred inorganic pigments are metal oxides and/or other metal compounds which are insoluble or sparingly soluble in water, in particular oxides of titanium ($TiO_2$), zinc (ZnO), iron (e.g. $Fe_2O_3$), zirconium ($ZrO_2$), silicon ($SiO_2$), manganese (e.g. MnO), aluminium ($Al_2O_3$), cerium (e.g. $Ce_2O_3$), mixed oxides of the corresponding metals, and mixtures of such oxides, and the sulphate of barium ($BaSO_4$).

For the purposes of the present invention, the pigments can advantageously also be used in the form of commercially available oily or aqueous predispersions. Dispersion auxiliaries and/or solubilization promoters may advantageously be added to these predispersions.

According to the invention, the pigments may advantageously be surface-treated ("coated"), the aim being to form and/or retain, for example, a hydrophilic, amphiphilic or hydrophobic character. This surface treatment can consist in providing the pigments with a thin hydrophilic and/or hydrophobic inorganic and/or organic layer by methods known per se. The various surface coatings can also comprise water for the purposes of the present invention.

Inorganic surface coatings for the purposes of the present invention may consist of aluminium oxide ($Al_2O_3$), aluminium hydroxide $Al(OH)_3$, and aluminium oxide hydrate (also: Alumina, CAS No.: 1333-84-2), sodium hexametaphosphate ($NaPO_3)_6$, sodium metaphosphate $(NaPO3)_n$, silicon dioxide ($SiO_2$) (also: Silica, CAS No.: 7631-86-9), barium sulphate ($BaSO_4$) or iron oxide ($Fe_2O_3$). These inorganic surface coatings can occur on their own, in combination and/or in combination with organic coating materials.

Organic surface coatings for the purposes of the present invention may consist of vegetable or animal aluminium stearate, vegetable or animal stearic acid, lauric acid, dimeth-ylpolysiloxane (also: dimethicone), methylpolysiloxane (methicone), simethicone (a mixture of dimethylpolysilox-ane with an average chain length of from 200 to 350 dimeth-ylsiloxane units and silica gel), or alginic acid. These organic surface coatings can appear on their own, in combination and/or in combination with inorganic coating materials.

Zinc oxide particles and predispersions of zinc oxide particles which are suitable according to the invention are obtainable under the following trade names from the companies listed:

| Trade name | Coating | Manufacturer |
|---|---|---|
| Z-Cote HP1 | 2% Dimethicone | BASF |
| Z-Cote | | BASF |
| ZnO NDM | 5% Dimethicone | H&R |
| MZ-505S | 5% Methicone | Tayca Corporation |

Suitable titanium dioxide particles and predispersions of titanium dioxide particles are available under the following trade names form the companies listed:

| Trade name | Coating | Manufacturer |
|---|---|---|
| MT-100TV | Aluminium hydroxide/stearic acid | Tayca Corporation |
| MT-100Z | Aluminium hydroxide/stearic acid | Tayca Corporation |
| Eusolex T-2000 | Alumina/Simethicone | Merck KgaA |
| Titanium dioxide T805 (Uvinul TiO$_2$) | Octyltrimethylsilane | Degussa |

Advantageous UV-A filter substances for the purposes of the present invention are dibenzoylmethane derivatives, in particular 4-(tert-butyl)-4'-methoxydibenzoylmethane (CAS No. 70356-09-1), which is sold by Givaudan under the name Parsol® 1789 and by Merck under the trade name Eusolex® 9020.

Advantageous further UV filter substances for the purposes of the present invention are sulphonated, water-soluble UV filters, such as, for example:

Phenylene-1,4-bis(2-benzimidazyl)-3.3'-5,5'-tetrasulphonic acid and its salts, particularly the corresponding sodium, potassium or triethanolammonium salts, in particular the phenylene-1,4-bis(2-benzimidazyl)-3,3'-5,5'-tetrasulphonic acid bis-sodium salt with the INCI name Disodium Phenyl Dibenzimidazole Tetrasulfonate (CAS No.: 180898-37-7), which is available, for example, under the trade name Neo Heliopan AP from Haarmann & Reimer;

Salts of 2-phenylbenzimidazole-5-sulphonic acid, and its sodium, potassium or its triethanolammonium salt, and the sulphonic acid itself with the INCI name Phenylbenzimidazole Sulfonic acid (CAS No. 27503-81-7), which is available, for example, under the trade name Eusolex 232 from Merck or under Neo Heliopan Hydro from Haarmann & Reimer;

1,4-Di(2-oxo-10-sulfo-3-bomylidenemethyl)benzene (also: 3,3'-(1,4-phenylenedimethylene)bis(7,7-dimethyl-2-oxobicyclo[2.2.1]hept-1-ylmethane sulphonic acid) and its salts (particularly the corresponding 10-sulfato compounds, in particular the corresponding sodium, potassium or tirethanolammonium salt), which is also referred as benzene-1,4-di(2-oxo-3-bomylidenemethyl-10-sulphonic acid). Benzene-1,4-di(2-oxo-3-bomylidenemethyl-10-sulphonic acid) has the INCI name Terephthalidene Dicamphor Sulphonic Acid (CAS No.: 90457-82-2) and is available, for example, under the trade name Mexoryl SX from Chimex;

Sulphonic acid derivatives of 3-benzylidenecamphor, such as, for example, 4-(2-oxo-3-bomylidenemethyl)benzenesulphonic acid, 2-methyl-5-(2-oxo-3-bomylidenemethyl)sulphonic acid and salts thereof;

Hydroxybenzophenonone derivatives, such as, for example, 2-(4-diethylamino-2-hyroxybenzoyl)benzoic acid hexyl ester, which is available, for example, from BASF under the trade name Uvinul® A Plus; and Benzoxozole derivatives, such as, for example, 2,4-bis[5-1 (dimethylpropyl)benzoxazol-2-yl-(4-phenyl)imino]-6-(2-ethylhexyl)imino-1,3,5-triazine (CAS No.: 288254-16-0), which is available, for example, under the trade name UVASorb® K2A from 3V Sigma.

Advantageous UV filter substances for the purposes of the present invention are also so-called broadband filters, i.e. filter substances which absorb both UV-A and also UV-B radiation. Advantageous broadband filters or UV-B filter substances are, for example, triazine derivatives, such as, for example:

2,4-bis {[4-(2-ethylhexyloxy)-2-hydroxy]phenyl}-6-(4-methoxyphenyl)-1,3,5-triazine (INCI: Aniso Triazine), which is available under the trade name Tinosorb® S from CIBA-Chemikalien GmbH;

diethylhexylbutylamidotriazone (INCI: Diethylhexylbutamidotriazone), which is available under the trade name UVASORB HEB from Sigma 3V; and tris(2-ethylhexyl) 4,4',4''-(1,3,5-triazine-2,4,6-triyltriimino)trisbenzoate, also: 2,4,6-tris[anilino(p-carbo-2'-ethyl-1'-hexyloxy)]-1,3,5-triazine (INCI: Ethyhexyl Triazone), which is sold by BASF Aktiengesellschaft under the trade name UVINUL® T 150.

An advantageous broadband filter for the purposes of the present invention is also 2,2'-methylenebis(6-(2H-benzotriazol-2-yl)-4-(1,1,3,3-tetramethylbutyl)phenol), which is available under the trade name Tinosorb® M from CIBA-Chemikalien GmbH. An advantageous broadband filter for the purposes of the present invention is also 2-(2H-benzotriazol-2-yl)-4-methyl-6-[2-methyl-3-[1,3,3,3-tetramethyl-1-[(trimethylsilyl)oxy]-disiloxanyl]propyl]phenol (CAS No.: 155633-54-8) with the INCI name Drometrizole Trisiloxane, which is available under the trade name Mexoryl® XL from Chimex.

The further UV filter substances may be oil-soluble or water-soluble. Advantageous oil-soluble UV-B and/or broadband filter substances for the purposes of the present invention are, for example:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino)benzoate;

derivatives of benzophenone, preferably 2-hydroxy-4-methoxybenzophenone, 2-hydroxy-4-methoxy-4'-methylbenzophenone, 2,2'-dihydroxy-4-methoxy-benzophenone;

UV filters bonded to polymers; and 3-(4-(2,2-bisethoxycarbonylvinyl)phenoxy)propenyl) methoxy-siloxane/dimethylsiloxane copolymer, which is available, for example, under the trade name Parsol® SLX from Hoffmann La Roche.

The list of specified UV filters which can be used for the purposes of the present invention is not of course intended to be limiting.

The UV light protection filters advantageous according to the invention are preferably used in a concentration of from 0.1 to 30% by weight, in particular in a concentration of from 0.5 to 15% by weight, based on the total weight of the formulation.

According to the invention, the preparation according to the invention can advantageously comprise glitter substances and/or other effect substances.

Advantageous embodiments of the cosmetic preparation according to the invention are also characterized in that they comprise, as further constituents, opacifiers and/or pearlizing agents. According to the invention, opacifiers are here understood as meaning substances and substance mixtures which impart a cloudy emulsion-like appearance to the preparation. According to the invention, pearlizing agents are understood here as meaning substances and substance mixtures which impart an opalescent appearance to the preparation. According to the invention, it is also advantageous to use mixtures of opacifiers and pearlizing agents. Opacifiers/pearlizing agents and/or mixtures advantageous according to the invention are, inter alia:

PEG-3 distearate (e.g. CUTINA TS from Cognis);

a combination of glycol distearate, glycerol, laureth-4 and cocamidopropylbetaine (e.g. Euperlan PK 3000 and Euperlan PK 4000 from Cognis);

a combination of glycol distearate, cocoglucosides, glyceryl oleate and glyceryl stearate (e.g. Lamesoft™ Benz from Cognis); and styrene/acrylate copolymers (e.g. Acusol OP 301 from Rohm & Haas).

The preparation according to the invention can advantageously comprise one or more antioxidants. The antioxidants are advantageously chosen from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, aurothioglucose, propylthiouracil and other thiols (e.g. thioredoxine, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, alaninediacetic acid, flavonoids, polyphenols, catechins, vitamin C and derivatives (e.g. ascorbyl palmitate, Mg ascorbyl phosphate, ascorbyl acetate), tocopherols and derivatives (e.g. vitamin E acetate), and coniferyl benzoate of benzoin resin, rutinic acid and derivatives thereof, ferulic acid and derivatives thereof, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of these specified active ingredients which are suitable according to the invention.

The amount of antioxidants (one or more compounds) in the preparations is preferably 0.001 to 10% by weight, particularly preferably 0.025-2.0% by weight, in particular 0.05-1.0% by weight, based on the total weight of the preparation.

Apart from the abovementioned substances, the compositions according to the invention optionally comprise the additives customary in cosmetics, for example perfume, dyes, antimicrobial substances, refatting agents, complexing agents and sequestering agents, pealizing agents, antidandruff active ingredients (e.g. selenium disulphide, zinc pyrithione, piroctone, olamine, climbazole, octopirox, polydocanol and combinations thereof), antiperspirant salts (e.g. acidic aluminium and/or aluminium/zirconium salts, such as aluminium chlorohydrate and/or aluminium/zirconium chlorohydrate), plant extacts, vitamins, active ingredients, peeling substances (abrasives, e.g. polymer beads or powders made of polyethylene, polypropylene etc. inorganic oxides, silicates etc.). In addition, hair-smoothing agents (e.g. thioglycolates) may be present in the preparation.

In particular, according to the invention it is advantageous to add vitamins, plant extracts and UV light protection filters to the preparation according to the invention. Thus, for example, the addition of calcium vitamin complexes (e.g. of γ-oryzanole and calcium salts such as calcium pantothenate, calcium chloride, calcium acetate) are particularly advantageous according to the invention.

Furthermore, the active ingredients according to the invention (one or more compounds) can also be chosen very advantageously from the group of hydrophilic active ingredients, in particular from the following group:

α-hydroxy acids such as lactic acid or salicylic acid, or salts thereof, such as, for example, Na lactate, Ca lactate, TEA lactate, urea, allantoin, serine, sorbitol, glycerol, milk proteins, panthenol, chitosan, polydocanol.

The list of specified active ingredients and/or active ingredient combinations which can be used in the preparations according to the invention is not of course intended to be limiting. The active ingredients can be used individually or in any combinations with one another.

The amount of such active ingredients (one or more compounds) in the preparations according to the invention is preferably 0.001 to 30% by weight, particularly preferably 0.05-20% by weight, in particular 1-10% by weight, based on the total weight of the preparation.

The active ingredients incorporated into the preparations according to the invention serve, inter alia, for the prophylaxis and/or treatment of inflammatory skin conditions and/or for protecting the skin in sensitively determined and dry skin (such as, for example, atopic eczema, seborrhoeic eczema, polymorphous photodermatosis, psoriasis, vitiligo, wound healing disorders, itching, sensitive or irritated skin, light-induced skin damage and UV-induced immunosuppression, changes in desquamation, changes in the normal fibroblast and keratinocyte proliferation, changes in the normal fibroblast and keratinocyte differentiation of deficient sensitive or hypoactive skin conditions or deficient sensitive or hypoactive conditions of skin appendages and for reducing the thickness of the skin).

The preparations according to the invention are entirely satisfactory preparations in every respect, which are not limited to the selection of raw materials mentioned in this specification.

According to the invention, it is advantageous if the cosmetic preparation according to the invention is stored in a bottle or squeezable bottle and is applied from this. Accordingly, bottles or squeezable bottles which contain a preparation according to the invention are also in accordance with the invention.

According to the invention, the preparation according to the invention can advantageously be applied as impregnation to a substrate. The substrates according to the invention may be smooth or surface-structured. According to the invention, preference is given to surface-structured substrates.

The combination of the cosmetic and/or dermatological preparation according to the invention and an insoluble substrate is also in accordance with the invention.

In the case of the substrates according to the invention, the fabric can be formed by warp and weft, by mesh formation or by intertwining, and/or cohesive and/or adhesive joining of textile fibres. In this connection, it is preferred according to the invention if the substrate is a composite.

According to the invention, preference is given to using substrates in the form of wipes, which consist of nonwoven fabric, in particular of water-jet-consolidated and/or waterjet-impressed nonwoven. The substrates may also advantageously be implemented in the form of a ball, perforated nonwoven or net.

Such substrates can have macroimpressions in any desired pattern. The choice to be made depends firstly on the impregnation to be applied and secondly on the field of use in which the subsequent wipe is to be used.

It has proven advantageous for the wipe to have a weight of from 20 to 120 g/m$^2$, preferably from 30 to 80 g/m$^2$, particularly preferably 40 to 60 g/m$^2$ (measured at 20° C.±2° C. and at a room air humidity of 65%±5% for 24 hours).

The thickness of the substrate is preferably 0.2 mm to 2 mm, in particular 0.4 mm to 1.5 mm, very particularly preferably 0.6 mm to 0.9 mm.

Starting materials for the nonwoven material of the wipe which can be used are generally all organic and inorganic natural and synthetic-based fibre materials. Examples which may be given are viscose, cotton, cellulose, jute, hemp, sisal, silk, wool, polypropylene, polyester, polyethylene terephthalate (PET), aramid, nylon, polyvinyl derivatives, polyurethanes, polylactide, polyhydroxyalkanoate, cellulose esters and/or polyethylene, and also mineral fibres, such as glass fibres or carbon fibres. However, the present invention is not limited to the materials specified, it being possible instead to use a large number of further fibres for forming the nonwoven. For the purposes of the present invention, it is particularly advantageous if the fibres used are not water-soluble.

In an advantageous embodiment of the nonwoven, the fibres consist of a mixture of 60% to 80% viscose with 40% to 20% PET, in particular 70% viscose and 30% PET. A mixture of 70% viscose and 30% PET is particularly advantageous.

According to the invention, a nonwoven according to the invention can advantageously have a mixture of three different fibre materials. In such a case, a mixture of 40% to 80% viscose with 50% to 20% PET and 1 to 30% cotton is preferred. According to the invention, particular preference is given to a mixture of 40% viscose and 50% PET and 10% cotton. Also particularly advantageous are fibres of high-strength polymers, such as polyamide, polyester and/or highly drawn polyethylene.

Moreover, the fibres can also be coloured in order to be able to emphasize and/or enhance the visual attractiveness of the nonwoven. The fibres can additionally comprise UV stabilizers and/or preservatives.

The fibres used to form the wipe preferably have a water-absorption rate of more than 60 mm/[10 min] (measured using the EDANA test 10.1-72), in particular more than 80 mm/[10 min].

Furthermore, the fibres used to form the wipe preferably have a water-absorption capacity of more than 5 g/g (measured using the EDANA test 10.1-72), in particular more than 8 g/g.

Advantageous wipes for the purposes of the present invention have a tear strength of, in particular,

|  |  | [N/50 mm] |
| --- | --- | --- |
| in the dry state | machine direction | >60, preferably >80 |
|  | transverse direction | >20, preferably >30 |
| in the impregnated state | machine direction | >40, preferably >60 |
|  | transverse direction | >10 preferably >20 |

The expandability of advantageous wipes is preferably

| in the dry state | machine direction | 15% to 100%, preferably 20% to 50% |
| --- | --- | --- |
|  | transverse direction | 40% to 120%, preferably 50% to 85% |
| in the impregnated state | machine direction | 15% to 100%, preferably 20% to 40% |
|  | transverse direction | 40% to 120%, preferably 50% to 85% |

In a supply form of such substrates according to the invention that is special according to the invention, the substrate can be dried following impregnation with the preparation and then be supplied to the user in the form of a dry cleansing wipe.

The preparation according to the invention can advantageously be stored in a foam dispenser and be applied from this. The foam dispenser may, according to the invention, advantageously be a mechanical pump dispenser (pump roamer) or an aerosol can. According to the invention, the preparations according to the invention can advantageously be foamed using a propellant gas. According to the invention, this is used in an amount of from 0.5 to 20% by weight, particularly advantageously in an amount of from 5 to 15% by weight and very particularly advantageously in an amount of from 8 to 11% by weight, in each case based on the total weight of the formulation. Propellant gases which are particularly advantageous according to the invention are propane, isobutane and n-butane, and mixtures thereof.

The person skilled in the art is of course aware that there are propellant gases which are non-toxic per se which in principle would be suitable for realizing the present invention in the form of aerosol preparations, but which nevertheless should be omitted because of an unacceptable impact on the environment or other accompanying circumstances, in particular fluorocarbons and chlorofluorocarbons (CFCs).

The use of the cosmetic and/or dermatological preparation according to the invention for the cleansing and/or care of the skin and skin appendages is in accordance with the invention. The use of the cosmetic and/or dermatological preparation according to the invention as shower bath, foam bath and/or tub bath is in accordance with the invention. The use of the cosmetic and/or dermatological preparation according to the invention as hair shampoo is in accordance with the invention. The use of the cosmetic and/or dermatological preparation as face-cleansing preparation for removing decorative cosmetics is in accordance with the invention.

The use of the cosmetic and/or dermatological preparation for the cleaning and washing of items of clothing and textiles ("detergents") is in accordance with the invention. The use of the cosmetic and/or dermatological preparation according to the invention for cleaning articles of daily life (e.g. dishes, table and cupboard surfaces, cars) is in accordance with the invention.

The use of the cosmetic and/or dermatological preparation for the cleaning and care of furs and coats of mammals, in particular of domestic and useful animals (e.g. dogs, cats, rodents, horses, cows, etc.) is in accordance with the invention.

The use of the cosmetic and/or dermatological preparation according to the invention for controlling aphids and scale insects, in particular when these are on the leaves of ornamental and useful plants, is in accordance with the invention.

Last but not least, the use of the cosmetic and/or dermatological preparations for the prophylaxis and/or treatment of inflammatory skin conditions and/or for protecting the skin in cases of sensitively determined and dry skin is in accordance with the invention.

The examples below are intended to illustrate the present invention without limiting it. Unless stated otherwise, all of the amounts, proportions and percentages given are based on the weight and the total amount, or on the total weight of the preparations.

Formulation Examples

The prepared formulations can be prepared clear or, with the help of opacifiers and pearlizing agents, milky, white.

HAIR SHAMPOOS

|  | 1 | 2 | 3 | 4 | 5 | 6 |
|---|---|---|---|---|---|---|
| Sodium lauryl ether sulphate | 9 | 8 | 9 | 9 | 9 | 9 |
| Cocamidopropylbetaine | 4 | 5 | 3 | 4 | 2 | 4 |
| Disodium PEG-5 lauryl citrate sulphosuccinate | 3 | 3 | 3 | 2 | 5 | — |
| Alkyl polyglucoside | — | — | — | — | — | 3 |
| Thickener | — | — | 0.1 | 0.2 | 0.3 | 0.2 |
| Polyquaternium-10 | 0.3 | 0.1 | 0.1 | 0.3 | 0.1 | 0.1 |
| Guar hydroxypropyltrimonium chloride | 0.1 | 0.1 | 0.1 | 0.2 | 0.2 | — |
| Licochalcone A | 0.025 | 0.025 | 0.05 | 0.02 | 0.1 | 0.025 |
| PEG-3 distearate | 1.5 | 2 | 2 | 1.5 | 1.5 | — |
| Opacifier | — | — | — | 0.1 | 0.5 | — |
| Iminodisuccinic acid | 0.1 | 0.2 | 0.1 | 0.5 | 0.5 | 0.5 |
| PEG-40 hydrogenated castor oil | 0.2 | 0.2 | 0.2 | 0.2 | 0.2 | 0.4 |
| Niacinamide | 0.01 | — | — | — | — | — |
| Jojoba oil | — | 0.01 | — | — | — | — |
| Vitamin E acetate | — | — | 0.01 | — | — | — |
| Sea minerals | — | — | — | 0.01 | — | — |
| Panthenol | — | — | — | — | 0.01 | — |
| Sodium salicylate | 0.4 | 0.4 | 0.4 | 0.4 | 0.4 | 0.4 |
| Calcium chloride | — | — | — | — | — | 0.05 |
| Oryzanol | — | — | — | — | — | 0.05 |
| Sodium benzoate | 0.4 | 0.4 | 0.4 | 0.4 | 0.4 | 0.4 |
| Sodium chloride | 0.9 | 1.0 | 0.2 | — | — | 0.8 |
| Citric acid | q.s. | q.s. | q.s. | q.s. | q.s. | q.s. |
| Perfume | q.s. | q.s. | q.s. | q.s. | q.s. | q.s. |
| Water | ad 100 | ad 100 | ad 100 | ad 100 | ad 100 | ad 100 |

SKIN-CLEANSING GELS

|  | 1 | 2 | 3 | 4 | 5 |
|---|---|---|---|---|---|
| Sodium laureth sulphate | 13.2% | 11% | 9.5% | 11% | 9.5% |
| Cocamidopropylbetaine | 1.65% | 3.3% | 3.8% | 3.3% | 3.8% |
| PEG-7 glyceryl cocoate | — | — | — | 2.0% | 2.0% |
| Laureth-2 | — | — | — | 0.1% | — |
| PEG-90 glyceryl isostearate | — | — | — | 0.3% | — |
| Sodium cocoyl glutamate | 1.25% | 0.75% | 2.5% | 0.75% | 0.75% |
| PEG-40 hydrogenated castor oil | 0.50% | 0.50% | 0.5% | 0.50% | 0.50% |
| PEG-100 hydrogenated glyceryl palmitate | 0.50% | 0.50% | 0.5% | 0.50% | 0.50% |
| Licochalcone A | 0.025% | 0.025% | 0.05% | 0.02% | 0.1% |
| Polyquaternium-10 | 0.2% | — | 0.2% | — | — |
| Sodium benzoate | 0.45% | 0.45% | 0.45% | 0.45% | 0.45% |
| Sodium salicylate | 0.20% | 0.20% | 0.2% | 0.20% | 0.20% |
| Citric acid | 0.50% | 0.50% | 0.5% | 0.50% | 0.50% |
| Perfume | q.s. | q.s. | q.s. | q.s. | q.s. |
| Water | ad 100 | ad 100 | ad 100 | ad 100 | ad 100 |

LES-FREE SKIN CLEANSING GELS

|  | 1 | 2 | 3 |
|---|---|---|---|
| Sodium myreth sulphate | 5% | 4% | 6% |
| Lauryl glucoside | 2.5% | — | — |
| Decyl glucoside | — | 3% | — |
| Sodium cocoamphoacetate | 6.5% | 7% | 8% |
| PEG-200 hydrogenated glyceryl palmitate | 0.4% | 0.4% | 0.4% |
| PEG-40 hydrogenated castor oil | 1% | 1% | 1% |
| Diammonium citrate | 0.12% | 0.12% | 0.12% |
| Polyquaternium-10 | 0.2% | — | — |
| Licochalcone A | 0.025% | 0.025% | 0.025% |
| Sodium benzoate | 0.3% | 0.3% | 0.3% |
| Sodium salicylate | 0.2% | 0.2% | 0.2% |
| Citric acid | 1.2% | 1.2% | 1.2% |
| Perfume | q.s. | q.s. | q.s. |
| Water | ad 100 | ad 100 | ad 100 |

FACE-CLEANSING GELS

|  | 1 | 2 | 3 | 4 | 5 |
|---|---|---|---|---|---|
| Sodium myreth sulphate | 2% | 4% | 3% | 5% | 2% |
| Decyl glucoside | 2% | 2% | 4% | 1% | 4% |
| Cocoamdopropylbetaine | — | 2% | — | 1% | 1% |
| Carbopol 1382 | 0.3% | 0.6% | 0.5% | 1% | — |
| Acrylates copolymer | 0.3% | 0.5% | 0.2% | 0.2% | 1% |
| Sodium hydroxide | 0.5% | 0.5% | 0.5% | 0.5% | 0.5% |

-continued

FACE-CLEANSING GELS

| | | | | | |
|---|---|---|---|---|---|
| Glycerol | 5% | 10% | 5% | 10% | — |
| Na3HEDTA | 0.5% | 0.5% | 0.5% | 0.5% | 0.5% |
| Licochalcone A | 0.025% | 0.025% | 0.025% | 0.05% | 0.01% |
| Phenoxyethanol | 0.5% | 0.5% | 0.5% | 0.5% | 0.5% |
| Parabens | 0.2% | 0.2% | 0.2% | 0.2% | 0.2% |
| Perfume | q.s. | q.s. | q.s. | q.s. | q.s. |
| Water | ad 100 | ad 100 | ad 100 | ad 100 | ad 100 |

| | 6 | 7 | 8 | 9 | 10 |
|---|---|---|---|---|---|
| Sodium laureth sulphate | 2% | 2% | 7% | 7% | — |
| Methyl cocoyl taurate | 0.6% | 0.6% | 0.6% | 0.6% | 6% |
| Carbopol 980 | 1.2% | 1.2% | 1.2% | 0.5% | 0.6% |
| Sodium hydroxide | 0.5% | 0.5% | 0.5% | 0.5% | 0.5% |
| Glycerol | 2.0% | 2.0% | 2.0% | — | 2.0% |
| Licochalcone A | 0.025% | 0.025% | 0.025% | 0.05% | 0.01% |
| Xanthan gum | 0.25% | 0.1% | 0.25% | — | — |
| Phenoxyethanol | 0.5% | 0.5% | 0.5% | 0.5% | 0.5% |
| Parabens | 0.2% | 0.2% | 0.2% | 0.2% | 0.2% |
| Perfume | q.s. | q.s. | q.s. | q.s. | q.s. |
| Water | ad 100 | ad 100 | ad 100 | ad 100 | ad 100 |

SKIN-CLEANSING EMULSIONS

| | 1 | 2 | 3 | 4 | 5 |
|---|---|---|---|---|---|
| Paraffin oil | 46% | 14% | 20% | 20% | 25% |
| Soya oil | 24.3% | 36% | 20% | 20% | 25% |
| Sodium lauryl ether sulphate | 7.35% | 12.3% | 11% | 11% | 11% |
| Sodium benzoate | 0.3% | 0.3% | 0.3% | — | 0.3% |
| Sodium salicylate | 0.2% | 0.2% | 0.2% | — | 0.2% |
| Acrylates/C10–C30 alkyl acrylate crosspolymer | — | — | 1% | 1% | 0.8% |
| Licochalcone A | 0.025% | 0.025% | 0.05% | 0.02% | 0.1% |
| Sodium hydroxide | — | — | 0.2% | 0.2% | 0.2% |
| Phenoxyethanol | — | — | — | 0.5% | — |
| Parabens | — | — | — | 0.2% | — |
| Perfume | q.s. | q.s. | q.s. | q.s. | q.s. |
| Water | ad 100 | ad 100 | ad 100 | ad 100 | ad 100 |

SKIN-CLEANSING OILS

| | 1 | 2 | 3 |
|---|---|---|---|
| Soya oil | 40% | — | — |
| Castor oil | 14% | 14% | 9% |
| Sunflower oil | — | 54% | — |
| Wheatgerm oil | — | — | 37% |
| Zetesol 100 | 41% | 30% | 51% |
| Licochalcone A | 0.025% | 0.025% | 0.05% |
| Poloxamer 101 | 2% | 2% | 2% |
| Perfume, antioxidants, preservatives | q.s. | q.s. | q.s. |
| Water | ad 100 | ad 100 | ad 100 |

| | 4 | 5 |
|---|---|---|
| TIPA laureth sulphate | 34% | 36% |
| Castor oil | 30% | 30% |
| Cocamide DEA | 10% | 10% |
| PEG-40 sorbitan perisostearate | 10% | 15% |
| Soya oil | 9% | — |
| Propylene glycol | 2% | 9% |
| Licochalcone A | 0.025% | 0.025% |
| Water | 1% | — |
| Perfume, antioxidants, preservatives | q.s. | q.s. |

PUMP FOAMER

| | 1 | 2 | 3 | 4 |
|---|---|---|---|---|
| Sodium cocoyl glutamate | 2.5 | — | — | — |
| Sodium lauryl ether sulphate | — | 3.5 | — | — |
| Sodium lauroyl sarcosinate | — | — | 5 | — |
| Sodium myristyl ether sulphate | — | — | — | 4.5 |
| Decyl glucoside | 3 | 4 | — | — |
| Lauryl glucoside | — | — | 3 | 3 |
| Polyquaternium-10 | 0.1 | — | — | 0.1 |
| Guar hydroxypropyltrimonium chloride | — | 0.15 | — | — |
| Polyquaternium-22 | — | — | 0.2 | — |
| PEG-200 hydrogenated glyceryl palmitate | 0.5 | — | — | — |
| PEG-40 hydrogenated castor oil | 0.1 | 0.1 | 0.1 | 0.1 |
| PEG-100 hydrogenated glyceryl palmitate | — | 0.5 | — | 0.5 |
| Licochalcone A | 0.025 | 0.025 | 0.05 | 0.02 |
| Sodium benzoate | 0.5 | 0.5 | — | 0.5 |
| Sodium salicylate | — | 0.2 | — | 0.2 |
| Phenoxyethanol | — | — | 0.16 | — |
| Jojoba oil (Buxus chinensis) | 0.1 | — | — | — |
| Citric acid | q.s. | q.s. | q.s. | q.s. |
| Perfume | q.s. | q.s. | q.s. | q.s. |
| Water | add 100 | add 100 | add 100 | add 100 |

AFTER-FOAMING SKIN-CLEANSING FORMULATIONS

| | 1 | 2 | 3 | 4 | 5 |
|---|---|---|---|---|---|
| Hydroxypropyl starch phosphate ester (structure XL) | 1% | 2% | 5% | 1% | 7% |
| Sodium laureth sulphate | 18.0 | 12.0 | 8.0 | 6.0 | 10.0 |
| Sorbitol | 2.0 | 0 | 3.0 | 3.0 | 5.0 |
| Laureth-4 | 0 | 0 | 7.0 | 7 | 0 |
| Lanolin alcohol PEG15 | 7.0 | 0 | 0 | 0 | 4.0 |
| Isopropyl palmitate | 0 | 0 | 3.0 | 3.0 | 5.0 |
| Isopropyl myristate | 4.0 | 2.0 | 0 | 0 | 0 |
| Glycerol | 0 | 5.0 | 2.0 | 1.0 | 0 |
| Xanthan gum | 0.5 | 0.5 | 0 | 0 | 0 |
| Phenoxyethanol | 0.2 | 0 | 0.2 | 0 | 0 |
| Parabens | 0.7 | 0 | 0.5 | 0 | 0 |
| Sodium hydroxide | 0.5 | 0 | 0.1 | 0.1 | 0 |
| Na3HEDTA | 0.5 | 0 | 0.5 | 0 | 0 |
| Licochalcone A | 0.1 | 0.025 | 0.05 | 0.02 | 0.1 |
| Sodium benzoate | 0 | 0 | 0.0 | 0.5 | 0.5 |
| Citric acid | 0 | 0.2 | 0.5 | 0.5 | 0 |
| Polyquaternium-10 | 0 | 0 | 0.2 | 0.2 | 0.2 |
| Sodium salicylate | 0 | 0.5 | 0 | 0 | 0 |
| Dye | 0 | 0 | 0 | 0.5 | 0.3 |
| Gas/foaming agent | 10.0 | 5.0 | 12.0 | 9.0 | 15 |
| Perfume | q.s. | q.s. | q.s. | q.s. | q.s. |
| Water | ad 100 | ad 100 | ad 100 | ad 100 | ad 100 |

The invention claimed is:

1. A cosmetic cleansing composition, wherein the composition is present in a liquid or gel form and comprises an extract of Radix *Glycyrrhiza inflata* and one or more surfactants in an amount of from 5% to 50% by weight, based on a total weight of the composition, the one or more surfactants comprising at least 5% by weight of at least one anionic surfactant.

2. The composition of claim 1, wherein the composition comprises at least 10% by weight of the one or more surfactants.

3. The composition of claim 1, wherein the composition comprises from 5% to 12% by weight of at least one anionic surfactant.

4. The composition of claim 1, wherein the composition is present as a shampoo.

5. The composition of claim 1, wherein the composition is present as a shower gel or as a foam bath.

6. The composition of claim 1, wherein the composition is present as a skin-cleansing gel.

7. The composition of claim 1, wherein the composition is present as a hand-washing lotion.

8. The composition of claim 1, wherein the composition comprises from 0.0001% to 5% by weight of an extract of Radix *Glycyrrhiza inflate*, based on the total weight of the composition.

9. The composition of claim 1, wherein the composition further comprises one or more saccharides.

10. The composition of claim 1, wherein the composition comprises one or more amphoteric surfactants in an amount of from 1% to 20% by weight, based on a total weight of the preparation.

11. The composition of claim 1, wherein the one or more surfactants comprise sodium laureth sulfate.

12. The composition of claim 1, wherein the one or more surfactants comprise sodium laureth sulfate and cocoamidopropyl betaine.

13. The composition of claim 1, wherein the composition is impregnated on an insoluble substrate in a form of a wipe, a ball, a perforated nonwoven or a net.

14. The composition of claim 1, wherein the extract of Radix *Glycyrrhiza inflata* comprises an alcoholic extract.

15. The composition of claim 1, wherein the extract of Radix *Glycyrrhiza inflata* comprises an aqueous extract.

16. A cosmetic cleansing composition, wherein the composition is present in a liquid or gel form and comprises from 0.005% to 2% by weight of an extract of Radix *Glycyrrhiza inflata* and from 5% to 30% by weight of one or more surfactants, each based on a total weight of the composition, the one or more surfactants comprising at least one amphoteric surfactant and at least 5% by weight of at least one anionic surfactant.

17. The composition of claim 16, wherein the composition comprises from 5% to 12% by weight of at least one anionic surfactant.

18. The composition of claim 17, wherein the composition comprises at least 10% by weight of the one or more surfactants.

19. The composition of claim 16, wherein the composition comprises the at least one amphoteric surfactant in an amount of from 2% to 10% by weight, based on a total weight of the preparation.

20. The composition of claim 16, wherein the composition comprises from 0.01% to 0.1% by weight of the extract of Radix *Glycyrrhiza inflata*.

21. The composition of claim 20, wherein the extract of Radix *Glycyrrhiza inflata* comprises an alcoholic extract.

22. The composition of claim 21, wherein the one or more surfactants comprise sodium laureth sulfate and cocoamidopropyl betaine.

23. The composition of claim 16, wherein the composition further comprises one or more saccharides.

* * * * *